(12) United States Patent
Chung

(10) Patent No.: US 10,307,151 B2
(45) Date of Patent: Jun. 4, 2019

(54) RETRACTOR FOR SURGICAL OPERATION

(71) Applicant: WECAN MEDICARE CO., LTD., Dongan-gu, Anyang-si, Gyeonggi-do (KR)

(72) Inventor: Chang Won Chung, Anyang-si (KR)

(*) Notice: Subject to any disclaimer, the term of this patent is extended or adjusted under 35 U.S.C. 154(b) by 0 days.

(21) Appl. No.: 15/751,927

(22) PCT Filed: Mar. 24, 2016

(86) PCT No.: PCT/KR2016/002968
§ 371 (c)(1),
(2) Date: Feb. 12, 2018

(87) PCT Pub. No.: WO2017/030264
PCT Pub. Date: Feb. 23, 2017

(65) Prior Publication Data
US 2018/0296206 A1 Oct. 18, 2018

(30) Foreign Application Priority Data
Aug. 19, 2015 (KR) .................. 10-2015-0116534

(51) Int. Cl.
*A61B 17/02* (2006.01)
(52) U.S. Cl.
CPC .......... *A61B 17/0293* (2013.01); *A61B 17/02* (2013.01)
(58) Field of Classification Search
CPC . A61B 17/02; A61B 17/0225; A61B 17/0287; A61B 17/0293
See application file for complete search history.

(56) References Cited

U.S. PATENT DOCUMENTS

| 2,586,488 | A | * | 2/1952 | Smith | A61B 17/0293 248/201 |
| 3,070,088 | A | * | 12/1962 | Brahos | A61B 17/0293 600/210 |
| 3,998,217 | A | * | 12/1976 | Trumbull | A61B 17/0293 600/233 |
| 4,430,991 | A | * | 2/1984 | Darnell | A61B 17/0293 600/217 |
| 5,769,783 | A | * | 6/1998 | Fowler | A61B 17/0293 600/226 |
| 5,785,649 | A | * | 7/1998 | Fowler, Jr. | A61B 17/0293 600/217 |
| 5,810,721 | A | * | 9/1998 | Mueller | A61B 17/0293 600/200 |

(Continued)

*Primary Examiner* — Eduardo C Robert
*Assistant Examiner* — Michelle C Eckman
(74) *Attorney, Agent, or Firm* — Patshegen IP LLC; Moshe Pinchas

(57) ABSTRACT

The present invention relates to a surgical traction device and, more specifically, to a surgical traction device, in which a surgical incision site is expanded to allow a surgical tool to be easily inserted in a state, in which the epidermis is incised for surgical operation, and an expansion part having elasticity is formed into a cylindrical shape and held on a fixing part at the upper portion thereof so as to maintain the incision site in an expanded state.

According to the present invention, the expansion part made of a material with elasticity can be inserted in the incision site so as to form a space for surgical operation and the expansion part can be easily attached to or separated from the fixing part so that it is easy to change the position of the traction device or remove the traction device during surgery.

3 Claims, 6 Drawing Sheets

(56) References Cited

U.S. PATENT DOCUMENTS

| | | | | |
|---|---|---|---|---|
| 6,048,309 A * | 4/2000 | Flom | A61B 17/0293 | 600/206 |
| 6,254,533 B1 * | 7/2001 | Fadem | A61B 17/0293 | 600/208 |
| 6,450,983 B1 * | 9/2002 | Rambo | A61B 17/0293 | 600/206 |
| 6,464,634 B1 * | 10/2002 | Fraser | A61B 17/0293 | 600/233 |
| 6,572,541 B1 * | 6/2003 | Petersvik | A61B 17/0293 | 600/231 |
| 6,814,700 B1 * | 11/2004 | Mueller | A61B 17/0293 | 600/201 |
| 2003/0004401 A1 * | 1/2003 | Ball | A61B 17/0293 | 600/233 |
| 2004/0073090 A1 * | 4/2004 | Butler | A61B 17/0293 | 600/208 |
| 2005/0209510 A1 * | 9/2005 | Bonadio | A61B 90/35 | 600/208 |
| 2005/0215865 A1 * | 9/2005 | LeVahn | A61B 17/0206 | 600/231 |
| 2005/0283050 A1 * | 12/2005 | Gundlapalli | A61B 17/0293 | 600/208 |
| 2007/0156023 A1 * | 7/2007 | Frasier | A61B 17/0293 | 600/206 |
| 2007/0238933 A1 * | 10/2007 | Alinsod | A61B 17/02 | 600/231 |
| 2008/0103366 A1 * | 5/2008 | Banchieri | A61B 1/32 | 600/208 |
| 2008/0234551 A1 * | 9/2008 | Lin | A61B 17/0293 | 600/235 |
| 2009/0082631 A1 * | 3/2009 | Cronin | A61B 17/02 | 600/201 |
| 2011/0021879 A1 * | 1/2011 | Hart | A61B 17/0293 | 600/207 |
| 2012/0130193 A1 * | 5/2012 | Haig | A61B 17/3423 | 600/210 |
| 2012/0289785 A1 * | 11/2012 | Albrecht | A61B 17/0293 | 600/208 |
| 2014/0276900 A1 * | 9/2014 | Cote | A61F 9/00736 | 606/107 |
| 2015/0018625 A1 * | 1/2015 | Miraki | A61B 17/0206 | 600/208 |
| 2015/0366548 A1 * | 12/2015 | Lauchner | A61B 17/0218 | 600/206 |
| 2016/0030239 A1 * | 2/2016 | Akura | A61B 17/0231 | 606/107 |
| 2016/0051244 A1 * | 2/2016 | Akura | A61B 17/0293 | 600/236 |
| 2017/0224321 A1 * | 8/2017 | Kessler | A61B 17/00234 | |
| 2017/0224323 A1 * | 8/2017 | Rowe | A61B 17/0057 | |

* cited by examiner

RETRACTOR FOR SURGICAL OPERATION

TECHNICAL FIELD

The present invention relates to a surgical traction device and, more specifically, to a surgical traction device, in which a surgical incision site is expanded to allow a surgical tool to be easily inserted in a state, in which the epidermis is incised for surgical operation, and an expansion part having elasticity is formed into a cylindrical shape and held on a fixing part at the upper portion thereof, thereby maintaining the incision site in the expanded state.

BACKGROUND ART

In order to perform a surgical operation, the skin of a patient is incised and the operation is performed directly for an organ or a muscle. To this end, it is necessary to extend the incision site so that a surgical tool can be easily accessed while the skin is incised.

Generally, a silicone ring or plastic tube, which has elasticity, is placed in an incision site so as to expand the incision site by elasticity, or the incision site is opened by pulling the same with forceps or surgical latches from side to side.

FIG. 1 is a perspective view showing a structure of a traction device for an abdominal operation according to the prior art, and FIG. 2 is an exploded perspective view showing a blade fixing device used in the traction device of FIG. 1.

The prior art traction device includes a vise 10 mounted at one corner of an operating table, a support device 20 mounted on the upper portion of the vise 10, a ring fixing device 30 fixed on the upper end of the support device 20, a ring 50 fixed on the ring fixing device 30 with one end thereof, a blade fixing device 60 held on the ring 50 in one direction so as to fix a blade in one direction, and the blade 70 inserted and fixed in the fixing device 60.

As for the prior art traction device 1 for an abdominal operation, the vise 10 includes two fixing members 13 and 14, which approach or depart from each other through guide members 11 and 12, and a fixing screw 15 for moving at least one of the fixing members along the guide members 11, 12.

The fixing member 13 at the upper portion is fixed on the guide member 11, which has a large diameter and an empty inside, and the guide member 12, which has a small diameter. The fixing member 14 at the lower portion moves along the guide members 11, 12 by the fixing screw 15, which is positioned at the lower side thereof, so as to be interlocked with the fixing member 13 at the upper portion. The upper fixing member 13 and the lower fixing member 14 are respectively provided with long concave portions 16 and 17, which are arranged at one side on the opposing surfaces thereof and coupled to one corner portion of the operating table at a distance from the corner portion. A fixing lever 18 is provided on one side surface of the upper fixing member 13 so as to fix one end portion of a first support of the support device inserted into the hollow guide member 13.

According to the conventional traction device 1 configured as above, the vise 10 is first mounted on one corner of the operating table and then the ring 50 is positioned according to the abdomen of an operation patient and fixed thereto by fastening several fixing screws. During the operation, the blade can be fixed with the blade fixing device at an appropriate position according to surgical conditions.

However, such a traction device is inconvenient to insert a laser scalpel, which is the most commonly used surgical tool, into an incision site so as to perform the surgery. Besides, it is difficult to contact the scalpel at the correct position due to the interference of the body part of the ring and the surgical tool, which meet each other.

DISCLOSURE

Technical Problem

Accordingly, the present invention has been made in an effort to solve the above-mentioned problems and disadvantages occurring in the prior arts, and it is an objective of the present invention to provide a surgical traction device, including a ring-shaped fixing part and an expansion part to be inserted into an incision site so as to expand the incision site outwards, wherein the fixing part is fixed in a state, in which a traction blade formed on the rim of the expansion part is pulled outwards, so as to prevent the expanded incision site from collapsing.

Technical Solution

A surgical traction device for extending an incision site formed in the epidermis for surgical operation, comprising: a fixing part to be seated on the upper surface of an incision site; and an expansion part passing through the fixing part and inserted into the incision site so as to open the incision site, wherein the fixing part includes a ring-shaped body, which has a through hole formed in the center of a disc, a traction blade seat part, which is formed to be concave on the surface thereof, and a fixing protrusion, which is formed to be protruded on the traction blade seat part, and wherein the expansion part includes an upper ring, in the center of which an epidermal opening is formed, a traction blade, which is formed to be protruded in a diameter direction on the outer rim of the upper ring, a side wall extending in the downward direction on the bottom surface of the inner rim of the upper ring, and a lower ring formed at the lower portion of the side wall.

The traction blade has one or two or more fixing grooves formed through the traction blade, and the fixing protrusions are inserted into the fixing grooves.

The expansion part is made of a silicon material.

Advantageous Effects

According to the present invention, the expansion part made of a material with elasticity can be inserted in the incision site so as to form a space for surgical operation and the expansion part can be easily attached to or separated from the fixing part so that it is easy to change the position of the traction device or remove the traction device during surgery.

MODE FOR INVENTION

Hereinafter, "a surgical traction device" hereinafter, referred to as "a traction device" according to each preferred embodiment of the present invention will be described in detail with reference to the accompanying drawings.

Figure 1:
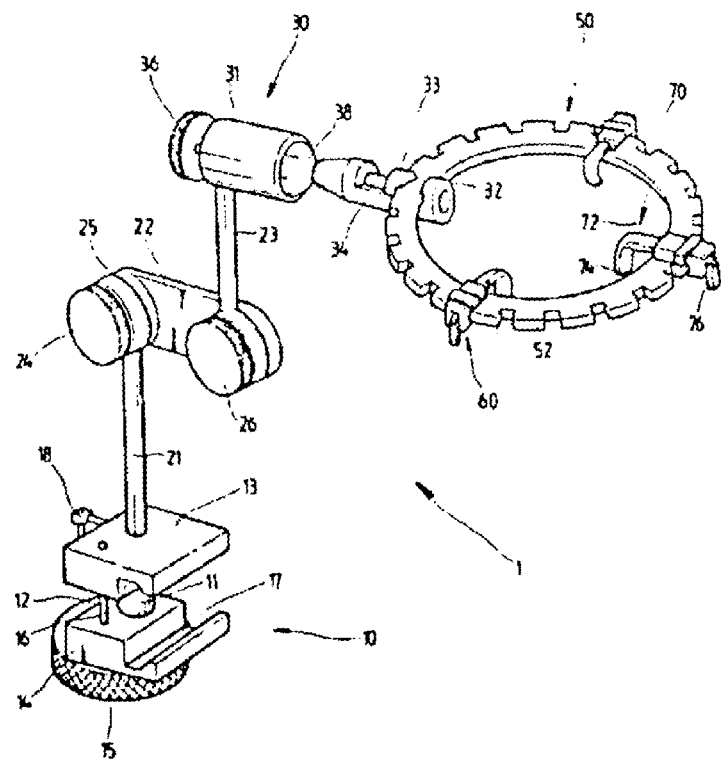
FIG. 1 is a perspective view showing a structure of a traction device for an abdominal operation according to the prior art.
Figure 2:
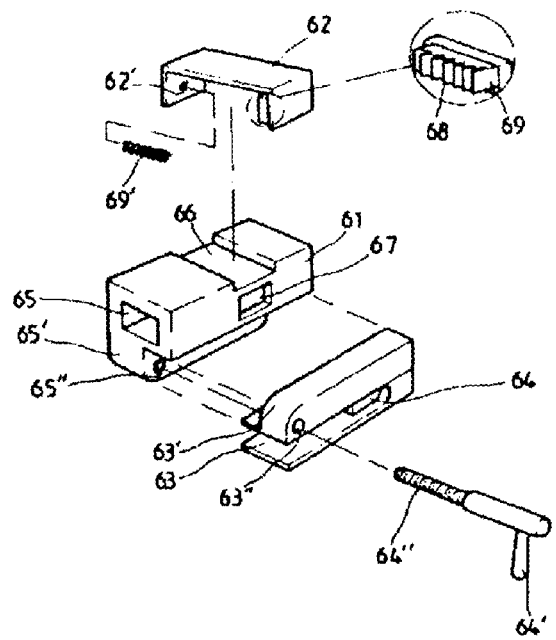
FIG. 2 is an exploded perspective view showing a blade fixing device used in the traction device of FIG. 1, FIG. 3 and FIG. 4 are perspective views illustrating a structure of a traction device according to an embodiment of the present invention.
Figure 3:
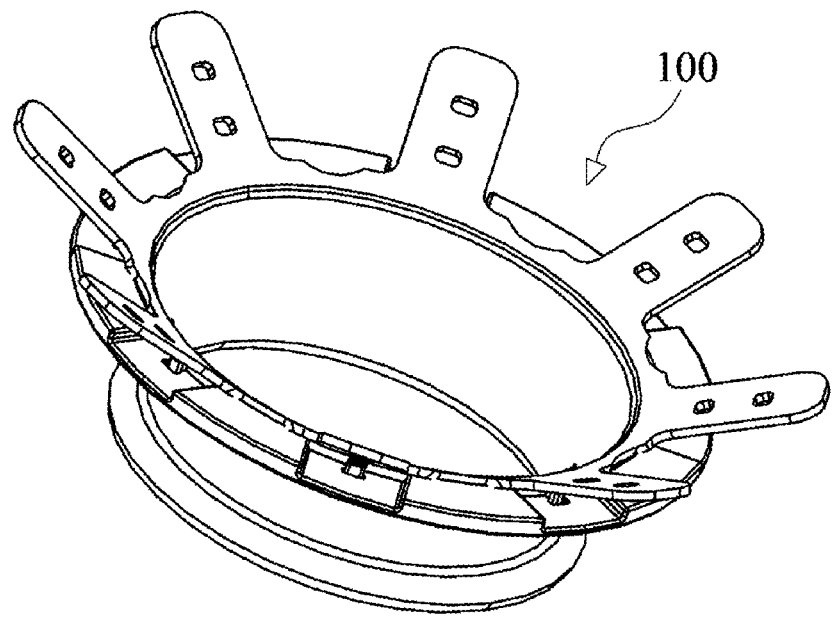
Figure 4:
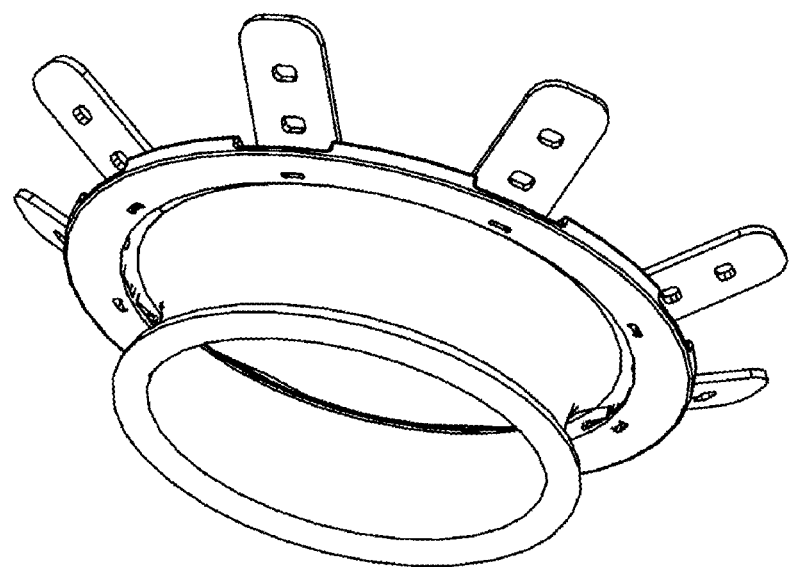
Figure 5:
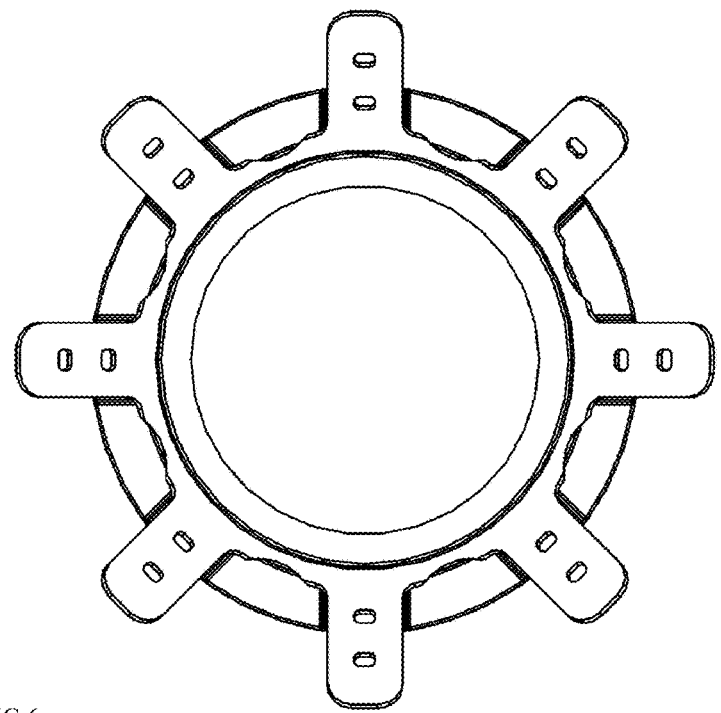
FIG. 5 is a plan view showing the structure of the traction device.
Figure 6:
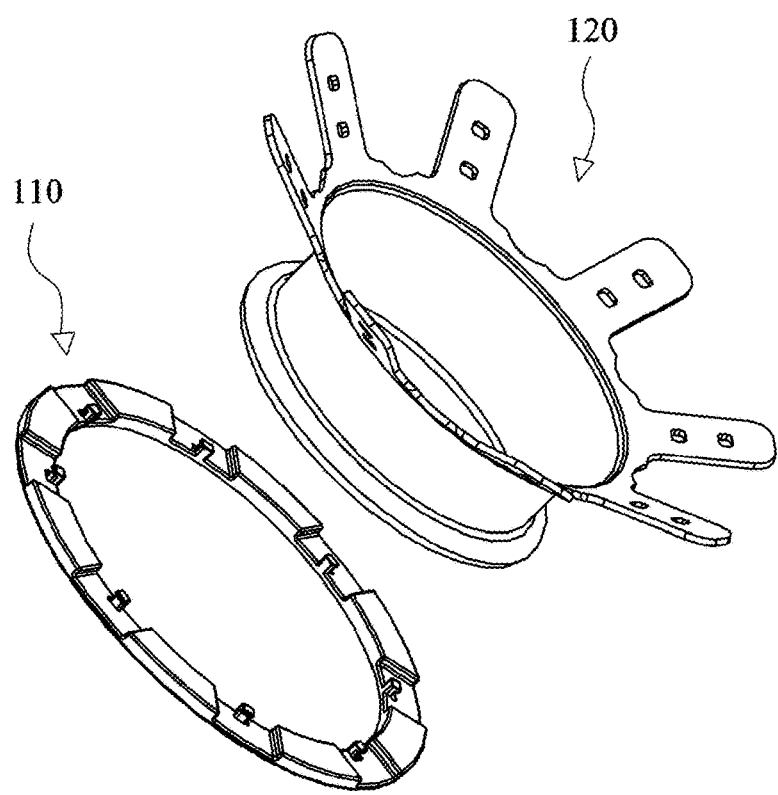
FIG. 6 is an exploded perspective view showing a state, in which a fixing part and an expansion part are separated from each other.

FIG. 3 and FIG. 4 are perspective views illustrating a structure of a traction device according to an embodiment of the present invention, FIG. 5 is a plan view showing the structure of the traction device, and FIG. 6 is an exploded perspective view showing a state, in which a fixing part and an expansion part are separated from each other.

A traction device 100 according to an embodiment of the present invention includes a fixing part 110 and an expansion part 120, wherein the fixing part 110 is made of a relatively rigid material and the expansion part 120 is made of a material with good flexibility.

The fixing part 110 has a ring-shaped body 111 formed in the center of a relatively thin disc and is determined by the size of an incision site, which is extended by the traction device 100. It is preferable that the inner opening has a diameter slightly larger than the size of the incision site.

Figure 7:
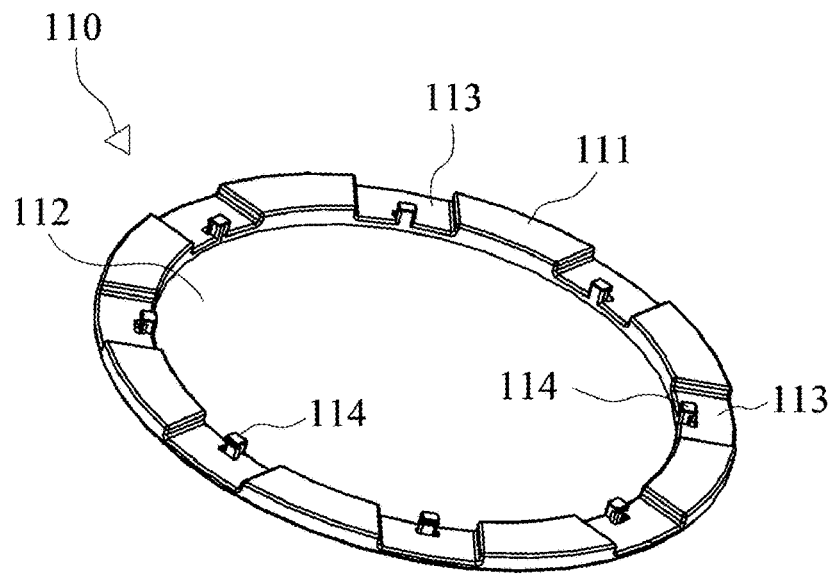
FIG. 7 is a perspective view showing the detailed structure of the fixing part.

FIG. 7 is a perspective view showing the detailed structure of the fixing part.

A circular through hole 112 is formed in the center of the ring-shaped body 111. In the drawings of the present invention, even though the shape of the through hole 112 is shown as being circular, it may be elliptical or polygonal in accordance with circumstances.

A number of traction blade seat parts 113 are recessed on the surface of the ring-shaped body 111. The traction blade seat parts 113 are generally formed at regular intervals, but the intervals may be irregular. A fixing protrusion 114 is protruded from the traction blade seat part 113. A concave groove is formed on the surface of the fixing protrusion 114, which is at the opposite side to the through hole 112.

The expansion part 120, which is made of a flexible material such as silicon, has a shape extending in the downward direction into a substantially cylindrical shape at the lower portion of the annular upper ring 121.

Figure 8:
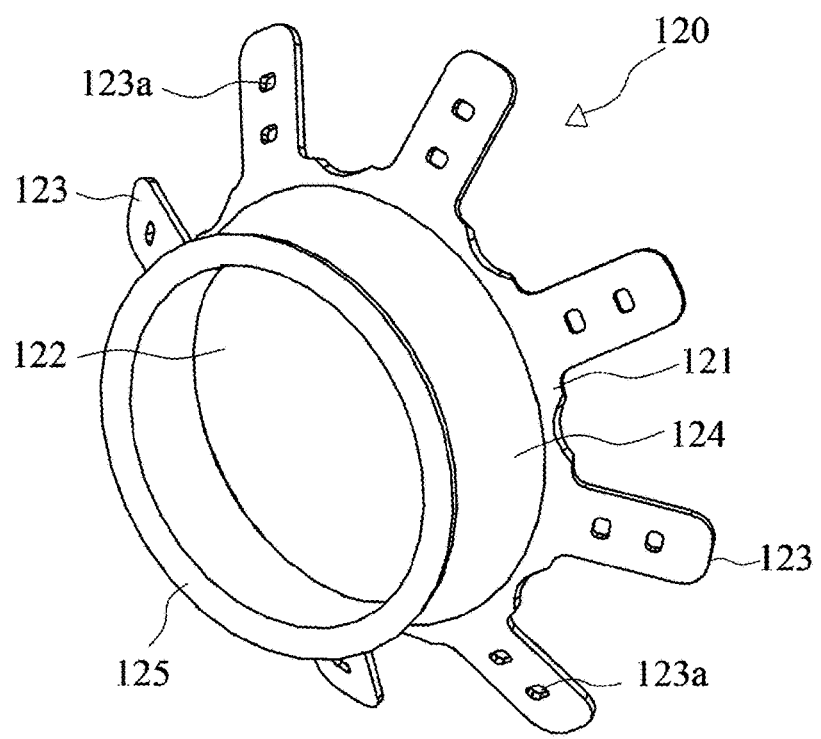
FIG. 8 is a perspective view showing the detailed structure of the expansion part.

FIG. 8 is a perspective view showing the detailed structure of the expansion part.

An epidermal opening 122 is formed in the center of the upper ring 121 and has a diameter similar to or slightly smaller than that of the through hole 112. Through the through hole 112 and the epidermal opening 122, surgical instruments can be accessed.

In the outer rim of the upper ring 121, several traction blades 123 are formed to be protruded in the diameter direction thereof. The traction blade 123 is a means for pulling the expansion part 120 outwards in the direction of the diameter thereof so as to allow the epidermal opening 122 to be expanded, and thus the traction blade 123 is formed to be protruded radially by a certain length. The traction blades 123 are formed with the same size as the traction blade seat parts 113 at the same intervals as those of the traction blade seat parts 113, wherein each of the traction blade 123 is fixed by the fixing protrusion 114 so that the traction blade 123 with elasticity does not return to the original position thereof.

The traction blade 123 is formed with one or two or more fixing grooves 123a penetrating therethrough. The fixing protrusions 114 are inserted into the fixing grooves 123a such that the fixing protrusions 114 and the fixing grooves 123a fix the traction blade 123 in a state, in which the traction blade 123 is pulled outwards. The fixing grooves 123a are arranged in the longitudinal direction of the traction blades 123, that is, in the diameter direction of the upper ring 121. The pulling degree of the traction blades 123 varies depending on the positions of the fixing grooves 123a, with which the fixing protrusions 114 are fitted. When the fixing protrusions 114 are fitted with the fixing grooves 123a at the innermost positions, which are closest to the center of the upper ring 121, the traction blades 123 are pulled farthest and thus the epidermal opening 122 is opened most. To the contrary, when the fixing protrusions 114 are fitted with the fixing grooves 123a at the outermost positions, the epidermal opening 122 is opened relatively small.

A side wall 124 is formed to be extended downwards on the bottom surface of the upper ring 121 at the inner rim thereof. The side wall 124 and the upper ring 121 are integrally formed with each other, and the side wall 124 forms a substantially cylindrical body. The side wall 124 is the portion, which comes into contact with the epidermis 200 during surgery.

The height of the side wall 124 is approximately equal to or slightly larger than the epidermis 200.

A lower ring 125 is formed at the lowest portion of the side wall 124. All of the upper ring 121, the side wall 124, the lower ring 125, and the traction blades 123 are injection-molded integrally since the lower ring 125 is also integrally formed with the side wall 124.

The lower ring 125 has a substantially circular or elliptical cross section in the circumferential direction thereof and is placed on the bottom surface of the epidermis 200 so as to prevent the expansion part 120 from moving away from the surgical site. To this end, the size of the lower ring 125 is formed to be slightly larger than the size of the incision site of the side wall 124.

Figure 9:
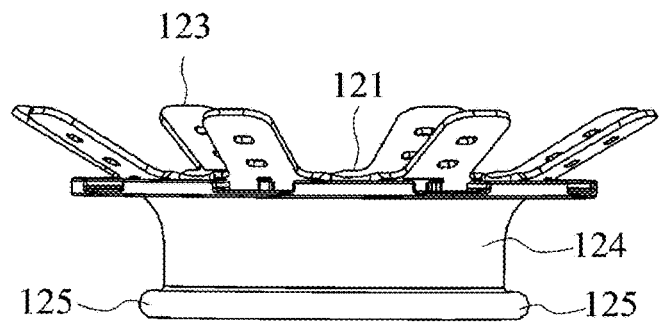
FIG. 9 is a side view showing a state, in which the fixing part and the expansion part are coupled to each other.

FIG. 9 is a side view showing a state, in which the fixing part and the expansion part are coupled to each other.

The expansion part 120 is inserted through the through hole 112 in the center of the fixing part 110. The fixing part 110 rises to approximately the same height as the upper ring 121, and the side wall 124 and the lower ring 125 are located at the lower side of the through hole 112. Herein, the fixing part 110 is positioned immediately under the traction blades 123 since the traction blades 123 are extended radially in a state, in which the traction blades 123 are flat or inclined obliquely with respect to the fixing part 110. Furthermore, each of the traction blades 123 is placed in each of the traction blade seat parts 113.

Figure 10:
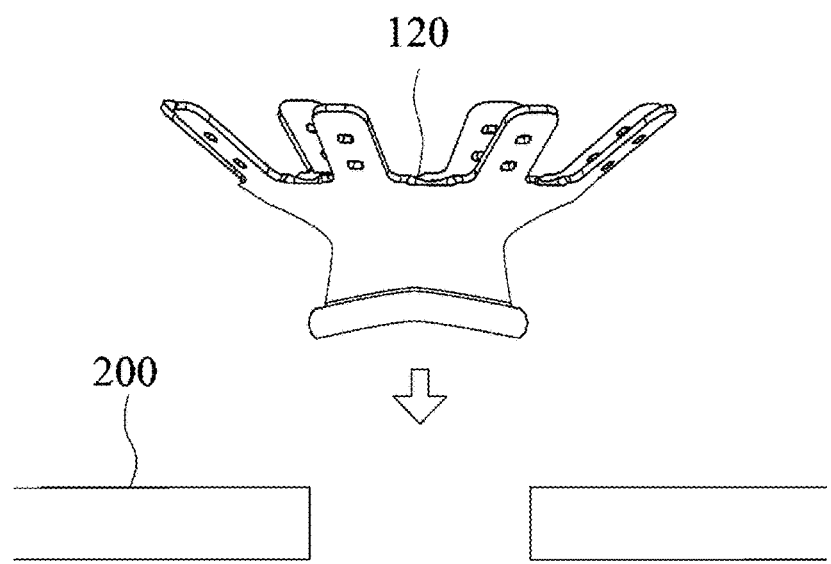
FIG. 10 is a side view showing a state, in which the expansion part is put in the incision site of the epidermis.
Figure 11:
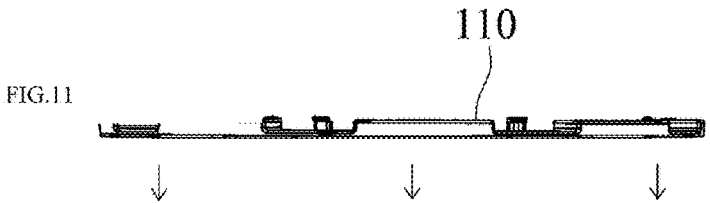
FIG. 11 is a side view showing the fitting of the fixing part with the expansion part, which has been put in the incision site.
Figure 11:
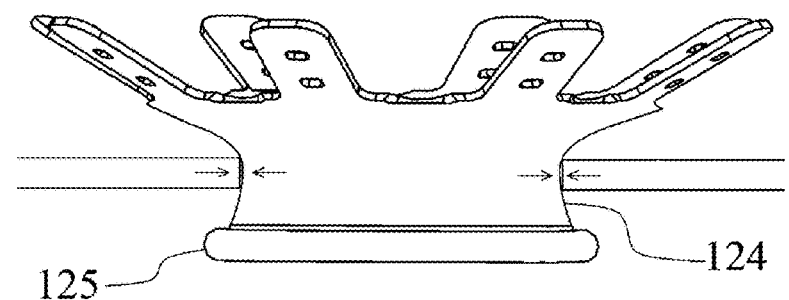
Figure 12:
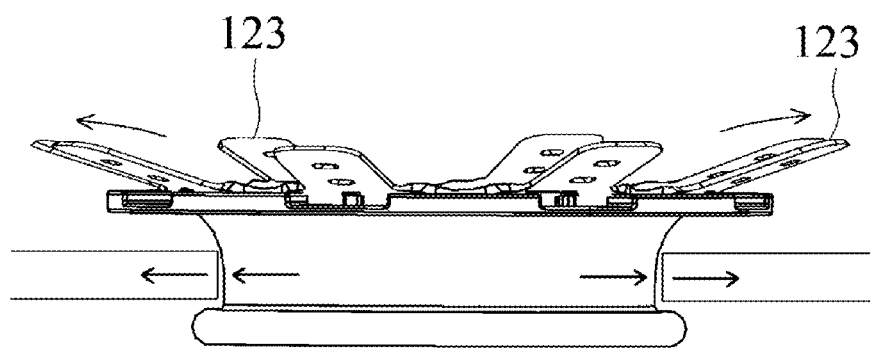
FIG. 12 is a side view showing the incision site, which is expanded by pulling the traction blade.

FIG. 10 is a side view showing a state, in which the expansion part is put in the incision site of the epidermis, FIG. 11 is a side view showing the fitting of the fixing part with the expansion part, which has been put in the incision site, and FIG. 12 is a side view showing the incision site, which is expanded by pulling the traction blade.

First, as shown in FIG. 10, the expansion part 120 is inserted into the incision area of the epidermis 200 for surgery. Because the expansion part 120 is made of a relatively flexible material, the lower ring 125 is slightly crushed and reduced in volume. Next, the lower ring 125 is placed under the epidermis 200 on the incision site.

The incision site has a shape close to a straight line before expansion, wherein, after the lower ring 125 is elongated, the epidermis 200 is slightly lifted and then the lower ring 125 is inserted beneath the same. The lower ring 125 is slightly expanded by the elasticity thereof and thus enters into the bottom surface of the epidermis 200. Therefore, the expansion part 120 is not immediately released to the outside.

Then, as shown in FIG. 11, the traction blades 123 of the expansion part 120 are slightly closed and inserted into the through hole 112 of the fixing part 110 in a state, in which the expansion part 120 is positioned beneath the epidermis 200. The fixing part 110 is positioned such that the traction blades 123 are positioned between the bottom surface and the surface of the epidermis 200.

In addition, as shown in FIG. 12, the fixing protrusions 114 are lowered and fitted with the fixing grooves 123a in a state, in which the traction blades 123 are pulled outwards. If the positions of the fixing grooves 123a are adjusted according to the size of the incision site, then the expansion part 120 can be opened outwards with appropriate force. In addition, if the incision site has a linear shape, it is also possible to expand the expansion part 120 by pulling the traction blades 123, which are located at the left and right sides with respect to the center of the fixing part 110.

A surgeon, who performs the procedure, inserts a surgical tool to the inside of the incision site through the through hole 112 and the epidermal opening 122. At the end of the operation, the surgeon raises the traction blades 123 and removes the fixing protrusions 114, which have been fitted with the fixing grooves 123a. When the fixing protrusions 114 are completely removed, the incision site narrows again as the upper ring 121 is gathered inwards. In addition, as opposed to the previously described, the surgeon removes the fixing part 110 by gathering the traction blades 123 of the expansion part 120 inwards, withdraws the lower ring 125 from the bottom surface of the epidermis, and then sutures the incision site in a state, in which the expansion part 120 is removed.

Although the preferred embodiments of the present invention have been described above with reference to the accompanying drawings, it would be understood that the invention may be implemented by a person skilled in the art, to which the present invention belongs, in other specific forms without changing the technical spirit or essential features of the invention. Therefore, it should be understood that the above-described embodiments are to be considered as illustrative and not restrictive, and that the scope of the present invention is defined by the appended claims rather than the foregoing description. Besides, it is intended that all changes or modifications derived from the meaning and scope of the claims and their equivalents be included within the scope of the present invention.

The invention claimed is:

1. A surgical traction device for extending an incision site formed in the epidermis (200) for surgical operation, comprising:
   a fixing part (110) configured to be seated on the upper surface of the epidermis; and
   an expansion part (120) made of a flexible material and being configured to passing through the fixing part (110) and configured to be inserted into the incision site so as to open the incision site, wherein the fixing part (110) includes
      a ring-shaped body (111) having a through hole (112) formed in the center of a disc,
      at least one traction blade seat part (113) formed as a recess on a surface of the ring-shaped body, and having a fixing protrusion (114) protruding from the traction blade seat part (113), and
   wherein the expansion part (120) includes
      an upper ring (121), in the center of which an epidermal opening (122) is formed,
      at least one traction blade (123) integrally formed with the upper ring and extending outwardly from the outer rim of the upper ring (121), and being configured to engage said at least one traction blade seat part and the fixing protrusion,
      a side wall (124) integrally formed with the upper ring and extending in the downward direction from the bottom surface of the inner rim of the upper ring (121) and being configured to be disposed inside the through hole (112) of the fixing part (110), and
      a lower ring (125) integrally formed at the lower portion of the side wall (124) and having a larger diameter than said side wall and being configured to engage a bottom surface of the epidermis such that the expansion part is held in the surgical site.

2. The surgical traction device according to claim 1, wherein one or two or more fixing grooves (123a) are formed through the traction blade (123) and the fixing protrusions (114) are inserted into the fixing grooves (123a).

3. The surgical traction device according to claim 1, wherein the expansion part (120) is made of a silicon material.

* * * * *